US007368102B2

(12) United States Patent
Tarara et al.

(10) Patent No.: US 7,368,102 B2
(45) Date of Patent: May 6, 2008

(54) PULMONARY DELIVERY OF AMINOGLYCOSIDES

(75) Inventors: Thomas E. Tarara, Burlingame, CA (US); Jeffry G. Weers, Half Moon Bay, CA (US); Geraldine Venthoye, Foster City, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 10/327,510

(22) Filed: Dec. 19, 2002

(65) Prior Publication Data
US 2003/0129140 A1 Jul. 10, 2003

Related U.S. Application Data

(60) Provisional application No. 60/342,827, filed on Dec. 19, 2001.

(51) Int. Cl.
*A61K 9/12* (2006.01)
*A61K 9/14* (2006.01)

(52) U.S. Cl. ............... 424/45; 424/46; 424/489; 514/34; 514/37; 514/39; 514/41

(58) Field of Classification Search ............... 424/45, 424/46, 489, 499, 450; 514/2, 34, 37, 39, 514/41
See application file for complete search history.

(56) References Cited

U.S. PATENT DOCUMENTS

| 3,014,844 | A | 12/1961 | Thiel et al. |
| 4,358,442 | A | 11/1982 | Wirtz-Peitz et al. |
| 4,397,799 | A | 8/1983 | Edgren et al. |
| 4,404,228 | A | 9/1983 | Cloosterman et al. |
| 4,571,334 | A | 2/1986 | Yoshida et al. |
| 4,590,206 | A | 5/1986 | Forrester et al. |
| 4,765,987 | A | 8/1988 | Bonte et al. |
| 4,818,542 | A | 4/1989 | DeLuca et al. |
| 4,904,479 | A | 2/1990 | Illum |
| 5,011,678 | A | 4/1991 | Wang et al. |
| 5,032,585 | A | 7/1991 | Lichtenberger |
| 5,069,936 | A | 12/1991 | Yen |
| 5,118,494 | A | 6/1992 | Schultz et al. |
| 5,126,123 | A | 6/1992 | Johnson |
| 5,145,684 | A | 9/1992 | Liversidge et al. |
| 5,173,298 | A | 12/1992 | Meadows |
| 5,182,097 | A | 1/1993 | Byron et al. |
| 5,190,029 | A | 3/1993 | Byron et al. |
| 5,208,226 | A | 5/1993 | Palmer |
| 5,225,183 | A | 7/1993 | Purewal et al. |
| 5,230,884 | A | 7/1993 | Evans et al. |
| 5,254,330 | A | 10/1993 | Ganderton et al. |
| 5,260,306 | A | 11/1993 | Boardman et al. |
| 5,262,405 | A | 11/1993 | Girod-Vaquez et al. |
| 5,284,656 | A | 2/1994 | Platz et al. |
| 5,299,566 | A | 4/1994 | Davis et al. |
| 5,306,483 | A | 4/1994 | Mautone |
| 5,308,620 | A | 5/1994 | Yen |
| 5,348,730 | A | 9/1994 | Greenleaf et al. |
| 5,376,359 | A | 12/1994 | Johnson |
| 5,437,272 | A | 8/1995 | Fuhrman |
| 5,451,569 | A | 9/1995 | Wong et al. |
| 5,470,885 | A | 11/1995 | Fuhrman et al. |
| 5,474,759 | A | 12/1995 | Fassberg et al. |
| 5,490,498 | A | 2/1996 | Faithfull et al. |
| 5,492,688 | A | 2/1996 | Byron et al. |
| 5,506,203 | A | 4/1996 | Bäckström et al. |
| 5,508,269 | A | 4/1996 | Smith et al. |
| 5,518,709 | A | 5/1996 | Sutton et al. |
| 5,518,731 | A | 5/1996 | Meadows |
| 5,518,998 | A | 5/1996 | Bäckström et al. |
| 5,527,521 | A | 6/1996 | Unger |
| 5,542,935 | A | 8/1996 | Unger et al. |
| 5,547,656 | A | 8/1996 | Unger |
| 5,562,608 | A | 10/1996 | Sekins et al. |
| 5,569,448 | A | 10/1996 | Wong et al. |
| 5,569,450 | A | 10/1996 | Duan et al. |
| 5,580,575 | A | 12/1996 | Unger et al. |
| 5,605,673 | A | 2/1997 | Schutt et al. |
| 5,605,674 | A | 2/1997 | Purewal et al. |
| 5,612,053 | A | 3/1997 | Baichwal et al. |
| 5,616,311 | A | 4/1997 | Yen |
| 5,635,159 | A | 6/1997 | Fu Lu et al. |
| 5,635,161 | A | 6/1997 | Adjei et al. |

(Continued)

FOREIGN PATENT DOCUMENTS

AU 714998 8/1997

(Continued)

OTHER PUBLICATIONS

J.M. Goldman et al., "Inhaled Micronised Gentamicin Powder: A New Delivery System," Thorax, BMJ Publishing Group, GB, vol. 45, No. 12, Dec. 1990, p. 939-940 XP001057935.
Ahlneck et al., "The molecular basis of moisture effect on the physical and chemical stability of drugs in the solid state", Inter. J. of Pharm., 62:87-95, (1990).
Altenbach et al., "$Ca^{2+}$ Binding to Phosphatidycholine Bilayers As Studied by Deuterium Magnetic Resonance. Evidence for the Formation of a $Ca^{2+}$ Complex with Two Phospholipid Molecules," Biochemistry, 23:3913-3920, ( 1999).

(Continued)

*Primary Examiner*—Mina Haghighatian
(74) *Attorney, Agent, or Firm*—Ashok K. Janah; Michael Mazza

(57) ABSTRACT

The present invention is directed to the administration of aminoglycosides. In particular, the present invention is directed to compositions and methods for the pulmonary administration of aminoglycosides. According to a preferred embodiment, compositions and methods are provided for the localized treatment of respiratory infections.

49 Claims, 4 Drawing Sheets

U.S. PATENT DOCUMENTS

| | | | |
|---|---|---|---|
| 5,648,095 A | 7/1997 | Illum et al. | |
| 5,653,961 A | 8/1997 | McNally et al. | |
| 5,653,962 A | 8/1997 | Akehurst et al. | |
| 5,654,007 A | 8/1997 | Johnson et al. | |
| 5,656,297 A | 8/1997 | Bernstein et al. | |
| 5,658,549 A | 8/1997 | Akehurst et al. | |
| 5,667,808 A | 9/1997 | Johnson et al. | |
| 5,667,809 A | 9/1997 | Trevino et al. | |
| 5,673,686 A | 10/1997 | Villax et al. | |
| 5,674,471 A | 10/1997 | Akehurst et al. | |
| 5,674,472 A | 10/1997 | Akehurst et al. | |
| 5,674,473 A | 10/1997 | Purewal et al. | |
| 5,676,929 A | 10/1997 | Akehurst et al. | |
| 5,681,545 A | 10/1997 | Purewal et al. | |
| 5,683,676 A | 11/1997 | Akehurst et al. | |
| 5,683,677 A | 11/1997 | Purewal et al. | |
| 5,688,782 A | 11/1997 | Neale et al. | |
| 5,690,954 A | 11/1997 | Illum | |
| 5,695,743 A | 12/1997 | Purewal et al. | |
| 5,695,744 A | 12/1997 | Neale et al. | |
| 5,698,537 A | 12/1997 | Pruss | |
| 5,707,352 A | 1/1998 | Sekins et al. | |
| 5,707,644 A | 1/1998 | Illum | |
| 5,718,222 A | 2/1998 | Lloyd et al. | |
| 5,718,921 A | 2/1998 | Mathiowitz et al. | |
| 5,720,940 A | 2/1998 | Purewal et al. | |
| 5,724,957 A | 3/1998 | Rubsamen et al. | |
| 5,725,841 A | 3/1998 | Duan et al. | |
| 5,725,871 A | 3/1998 | Illum | |
| 5,735,263 A | 4/1998 | Rubsamen et al. | |
| 5,736,124 A | 4/1998 | Akehurst et al. | |
| 5,741,478 A | 4/1998 | Osborne et al. | |
| 5,741,522 A | 4/1998 | Violante et al. | |
| 5,743,250 A | 4/1998 | Gonda et al. | |
| 5,743,252 A | 4/1998 | Rubsamen et al. | |
| 5,744,123 A | 4/1998 | Akehurst et al. | |
| 5,744,166 A | 4/1998 | Illum | |
| 5,747,001 A | 5/1998 | Wiedmann et al. | |
| 5,747,445 A | 5/1998 | Bäckström et al. | |
| 5,755,218 A | 5/1998 | Johansson et al. | |
| 5,756,104 A | 5/1998 | de Haan et al. | |
| 5,766,573 A | 6/1998 | Purewal et al. | |
| 5,770,187 A | 6/1998 | Hasebe et al. | |
| 5,770,222 A | 6/1998 | Unger et al. | |
| 5,770,559 A | 6/1998 | Manning et al. | |
| 5,770,585 A | 6/1998 | Kaufman et al. | |
| 5,776,496 A | 7/1998 | Violante et al. | |
| 5,804,212 A | 9/1998 | Illum | |
| 5,811,406 A | 9/1998 | Szoka, Jr. et al. | |
| 5,814,607 A | 9/1998 | Patton | |
| 5,817,293 A | 10/1998 | Akehurst et al. | |
| 5,820,883 A | 10/1998 | Tice et al. | |
| 5,829,435 A | 11/1998 | Rubsamen et al. | |
| 5,830,430 A | 11/1998 | Unger et al. | |
| 5,830,853 A | 11/1998 | Bäckström et al. | |
| 5,853,698 A | 12/1998 | Straub et al. | |
| 5,853,752 A | 12/1998 | Unger et al. | |
| 5,853,763 A | 12/1998 | Tice et al. | |
| 5,855,913 A | 1/1999 | Hanes et al. | |
| 5,856,367 A | 1/1999 | Barrows et al. | |
| 5,858,784 A | 1/1999 | Debs et al. | |
| 5,863,554 A | 1/1999 | Illum | |
| 5,874,063 A | 2/1999 | Briggner et al. | |
| 5,874,064 A | 2/1999 | Edwards et al. | |
| 5,875,776 A | 3/1999 | Vaghefi | |
| 5,891,844 A | 4/1999 | Häfner | |
| 5,898,028 A | 4/1999 | Jensen et al. | |
| 5,925,334 A | 7/1999 | Rubin et al. | |
| 5,955,143 A | 9/1999 | Wheatley et al. | |
| 5,972,388 A * | 10/1999 | Sakon et al. | 424/499 |
| 5,985,309 A | 11/1999 | Edwards et al. | |
| 5,994,318 A | 11/1999 | Gould-Fogerite et al. | |
| 6,017,310 A | 1/2000 | Johnson et al. | |
| 6,019,968 A | 2/2000 | Platz et al. | |
| 6,041,777 A | 3/2000 | Faithfull et al. | |
| 6,048,546 A | 4/2000 | Sasaki et al. | |
| 6,051,259 A | 4/2000 | Johnson et al. | |
| 6,068,600 A | 5/2000 | Johnson et al. | |
| 6,113,948 A | 9/2000 | Heath et al. | |
| 6,123,936 A * | 9/2000 | Platz et al. | 424/85.6 |
| 6,129,934 A | 10/2000 | Egan et al. | |
| 6,143,276 A | 11/2000 | Unger | |
| 6,165,597 A | 12/2000 | Williams et al. | |
| 6,315,983 B1 | 11/2001 | Eistetter | |
| 6,387,886 B1* | 5/2002 | Montgomery et al. | 514/34 |
| 6,514,482 B1* | 2/2003 | Bartus et al. | 424/45 |
| 6,518,239 B1* | 2/2003 | Kuo et al. | 514/2 |
| 2002/0187106 A1 | 12/2002 | Weers et al. | |
| 2003/0096774 A1* | 5/2003 | Gonda et al. | 514/44 |

FOREIGN PATENT DOCUMENTS

| | | |
|---|---|---|
| CA | 2036844 | 8/1991 |
| EP | 0 372 777 | 6/1990 |
| EP | 0 391 896 | 3/1994 |
| EP | 0 536 204 | 4/1994 |
| EP | 0 274 431 | 5/1994 |
| EP | 0 611 567 | 8/1994 |
| EP | 0 553 298 | 11/1994 |
| EP | 0 653 205 | 5/1995 |
| EP | 0 655 237 | 5/1995 |
| EP | 0 656 205 | 6/1995 |
| EP | 0 513 127 | 7/1995 |
| EP | 0 493 437 | 8/1995 |
| EP | 0 556 256 | 8/1995 |
| EP | 0 616 525 | 9/1995 |
| EP | 0 499 344 | 10/1995 |
| EP | 0 587 790 | 1/1996 |
| EP | 0 588 897 | 2/1996 |
| EP | 0 536 235 | 1/1997 |
| EP | 0 658 101 | 1/1998 |
| EP | 0 539 522 | 12/1998 |
| EP | 0 605 578 | 9/1999 |
| GB | 2 065 659 | 7/1981 |
| JP | 03038592 | 2/1991 |
| WO | 91/04011 | 4/1991 |
| WO | 91/11173 | 8/1991 |
| WO | 91/12823 | 9/1991 |
| WO | 91/16444 | 10/1991 |
| WO | 91/16882 | 11/1991 |
| WO | 92/00107 | 1/1992 |
| WO | 92/11050 | 7/1992 |
| WO | 92/14444 | 9/1992 |
| WO | 92/18164 | 10/1992 |
| WO | 93/11744 | 6/1993 |
| WO | 93/11745 | 6/1993 |
| WO | 93/14172 | 7/1993 |
| WO | 94/08552 | 4/1994 |
| WO | 94/08627 | 4/1994 |
| WO | 95/00128 | 1/1995 |
| WO | 95/05194 | 2/1995 |
| WO | 95/15118 | 6/1995 |
| WO | 95/17195 | 6/1995 |
| WO | 95/23613 | 9/1995 |
| WO | 95/24892 | 9/1995 |
| WO | 95/27476 | 10/1995 |
| WO | 95/28944 | 11/1995 |
| WO | 95/31182 | 11/1995 |
| WO | 95/31964 | 11/1995 |
| WO | 96/09814 | 4/1996 |
| WO | 96/15814 | 5/1996 |
| WO | 96/18388 | 6/1996 |
| WO | 96/19197 | 6/1996 |
| WO | 96/19198 | 6/1996 |

| | | |
|---|---|---|
| WO | 96/19199 | 6/1996 |
| WO | 96/19968 | 7/1996 |
| WO | 96/26746 | 9/1996 |
| WO | 96/32149 | 10/1996 |
| WO | 96/37399 | 11/1996 |
| WO | 96/40068 | 12/1996 |
| WO | 96/40277 | 12/1996 |
| WO | 97/03649 | 2/1997 |
| WO | 97/26863 | 7/1997 |
| WO | 97/35562 | 10/1997 |
| WO | 97/36574 | 10/1997 |
| WO | 97/36578 | 10/1997 |
| WO | 97/40819 | 11/1997 |
| WO | 97/41833 | 11/1997 |
| WO | 97/44012 | 11/1997 |
| WO | 97/44013 | 11/1997 |
| WO | 98/00111 | 1/1998 |
| WO | 98/01161 | 1/1998 |
| WO | 98/05302 | 2/1998 |
| WO | 98/07414 | 2/1998 |
| WO | 98/08519 | 3/1998 |
| WO | 98/13031 | 4/1998 |
| WO | 98/16205 | 4/1998 |
| WO | 98/17257 | 4/1998 |
| WO | 98/29097 | 7/1998 |
| WO | 98/29098 | 7/1998 |
| WO | 98/29099 | 7/1998 |
| WO | 98/29140 | 7/1998 |
| WO | 98/30207 | 7/1998 |
| WO | 98/31346 | 7/1998 |
| WO | 98/33480 | 8/1998 |
| WO | 98/33487 | 8/1998 |
| WO | 98/41188 | 9/1998 |
| WO | 99/06026 | 2/1999 |
| WO | 99/16419 | 4/1999 |
| WO | 99/16420 | 4/1999 |
| WO | 99/16421 | 4/1999 |
| WO | 99/16422 | 4/1999 |
| WO | 99/32083 | 7/1999 |
| WO | 00/00176 | 1/2000 |
| WO | 00/00215 | 1/2000 |
| WO | 01/13892 | 3/2001 |
| WO | WO 01/32144 | 5/2001 |
| WO | WO 01/85136 | 11/2001 |

OTHER PUBLICATIONS

Babincová et al., "Dextran Enhances Calcium-Induced Aggregation of Phosphatidylserine Liposomes: Possible Implications for Exocytosis", Physiol. Res., 48(4):319-321, (1999).
Ben-Jebraia et al., "Large Porous Particles for Sustained Protection from Carbachol-Induced Bronchoconstriction in Guinea Pigs", Pharm. Res., 16(4):555-561, (1999).
Buckton et al., "The use of gravimetric studies of assess the degree of crystallinity of predominantly crystalline powders", Int. J. of Pharm., 123:265-271, (1995).
Buldt et al., "Neutron Diffraction Studies on Phosphatidylcholine Model Membranes", J. Mol. Biol., 134:673-691, (1979).
Cevc, "Membrane Electrostatics", Biochimica et Biophysica Acta, 1031-3:311-382, (1990), in particular pp. 330-338.
Dellamary et al., "Hollow Porous Particles in Metered Dose Inhalers", Pharm. Res., 17(2):168-174, (2000).
Dunbar, "Dispersion and Characterization of Pharmaceutical Dry Powder Aerosols", Kona, No. 16, pp. 7-45, (1998).
Düzgünes et al., "Studies on the Mechanism of Membrane Fusion. Role of Head-Group Composition in Calcium-and-Magnesium-Induced Fusion of Mixed Phospholipid Vesicles", Biochimica et Biophysica Acta, 642:182-195, (1981).
Ebara et al., "Interactions of Calcium Ions with Phospholipid Membranes. Studies on π-A Isotherms and Electrochemical and Quartz-Crystal Microbalance Measurements[1]", Langmuir 10:2267-2271, (Apr. 1994).
Eisenberg et al., "Adsorption of Monovalent Cations to Bilayer Membranes Containing Negative Phospholipids", Biochemistry, 18(23):5213-5223, (1979).
Goldbach et al., "Spray-Drying of Liposomes for a Pulmonary Administration. I. Chemical Stability of Phospholipids", Drug Develop. Ind. Pharm., 19(19):2611-2622, (1993).
Gordon et al., "Ideal Copolymers and the Second-Order Transitions of Synthetic Rubbers. I. Non-Crystalline Copolymers", J. Appl. Chem., 2:493-500, (Sep. 1952).
Hancock et al., "Characteristics and Significance of the Amorphous State in Pharmaceutical Systems", J. of Pharm. Sci., 86(1):1-12, (Jan. 1997).
Hancock et al., "The Relationship Between the Glass Transition Temperature and the Water Content of Amorphous Pharmaceutical Solids", Pharm. Res., 11(4):471-477, (1994).
Hauser et al., "Comparative structural aspects of cation binding to phosphatidylserine bilayers", Biochimica Biophysica Acta, 813:343-346, (1985).
Hauser et al., Interactions of Divalent Cations with Phosphatidylserine Bilayer Membranes, Biochemistry, 23:34-41, (1984).
Huster et al., "Investigation of Phospholipid Area Compression Induced by Calcium-Mediated Dextran Sulfate Interaction", Biophys. J., 77(2):879-887, (Aug. 1999).
Huster et al., "Strength of $Ca^{2+}$ Binding to Rentinal Lipid Membranes: Consequences for Lipid Organization", Biophys. J. 78(6):3011-3018, (Jun. 2000).
Jacobson et al., "Phase Transitions and Phase Separations in Phospholipid Membranes Induced by Changes in Temperature, pH, and Concentration of Bivalent Cations", Biochemistry, 14(1):152-161, (1975).
Kwon et al., "Calcium Ion Adsorption on Phospholipid Bilayers-Theoretical Interpretation", J. Jap. Oil Chem. Soc., 43(1):23-30, (1994).
Lis et al., "Binding of Divalent Cations to Dipalmitoylphosphatidylcholine Bilayers and Its Effect on Bilayer Interaction", Biochemistry, 20:1761-1770, (1981).
Lis et al., "Adsorption of Divalent Cations to a Variety of Phosphatidylcholine Bilayers", Biochemisry, 20:1771-1777, (1981).
Millqvist-Fureby et al., "Spray-drying of trypsin—surface characterization and activity preservation", Int. J. Pharm., 188:243-253, (1999).
Millqvist-Fureby et al., "Surface characterization of freeze-dried protein/carbohydrate mixtures", Int. J. Pharm., 191:103-114, (1999).
Parasassi et al., "Calcium-Induced Phase Separation in Phospholipid Bilayers. A Fluorescence Anisotropy", Cellular and Molecular Biology, 32(3):261-266, (1986).
Reboiras, "Activity Coefficients of $CaCl_2$ and $MgCl_2$ in the presence of depalmitoylphosphatidylcholine-phosphatidylinositol vesicles in aqueous media", Bioelectrochemistry and Bioenergetics, 39:101-108, (1996).
Roth et al., "Production of Hollow Spheres", J. Aerosol Sci., 19(7):939-942, (1988).
Royall et al., "Characterisation of moisture uptake effects on the glass transitional behaviour of an amorhpous drug using modulated temperature DSC", Int. J. Pharm., 192:39-46, (1999).
Satoh, "Determination of binding constants of $Ca^{2+}$, $Na^+$, and $Cl^-$ ions to liposomal membranes of depalmitoylphosphatidylcholine at gel phase by particle electrophoresis", Biochimica Biophysica. Acta, 1239:239-248, (1995).
Seddon, "Structure of the inverted hexagonal ($H_{II}$) phase, and non-lamellar phase transitions of lipids", Biochimica Biophysica Acta, 1031:1-69, (1990), in particular pp. 43-44 and 49-50.
Seelig, "Metal Ion Interactions with Lipids", Handbook of Metal-Ligand Interactions in Biological Fluids, Bioinorganic Chemistry, vol. 1, Part 3, Chapter2, Sec. F, pp. 698-706, (1995).
Shah et al., "The ionic structure of sphingomyelin monolayers", Biochimica Biophysica Acta, 135:184-187, (1967).
Shavnin et al., "Cholesterol affects divalent cation-induced fusion and isothermal phase transitions of phospholipid membranes", Biochimica Biophysica Acta, 946:405-416, (1988).

Simha et al., "On a General Relation Involving the Glass Temperature and Coefficients of Expansion of Polymers", J. Chem. Physics., 37(5):1003-1007, (Sep. 1962).

Sugisaki et al., "Calorimetric Study of the Glassy State. IV. Heat Capacities of Glassy Water and Cubic Ice", Bulletin of the Chemical Society of Japan, 41:2591-2599, (Nov. 1968).

Tatulian, "Binding of alkaline-earth metal cations and some anions to phosphatidylcholine liposomes", Eur. J. Biochem., 170:413-420, (1987).

Verstraeten et al., "Effects of $Al^{3+}$ and Related Metals on Membrane Phase State and Hydration: Correlation with Lipid Oxidation", Arch. Biochem. Biophys., 375(2):340-346, (Mar. 15, 2000).

Whipps et al., "Growth of calcium monohydrate at phospholipid Langmuir monolayers", J. Crystal Growth, 192:243-249, (1998).

Yamaguchi et al., "Adsorption of divalent cations onto the membrane surface of lipid emulsion", Colloids and Surfaces B: Biointerfaces, 5:49-55, (1995).

Zarif et al., "Amphortericin B Cochleates as a Novel Oral Delivery System for the Treatment of Fungal Infections", Proceed. Int'l Symp. Control. Rel. Bioact. Mater., 26:964-965, (Revised Jul. 1999) Controlled Release Society, Inc.

* cited by examiner

FIG. 2

Tobramycin Sulfate PulmoSphere
Aerosol Characteristics in Turbospin at 60 LPM n=10

ED (%)

86.7 (3.9)   85.2 (2.0)   85.1 (1.3)   84.6 (1.3)   81.6 (2.2)

Capsule Fill Mass (mg)

FIG. 3

**Tobramycin Sulfate *PulmoSphere*™
Aerosol Characteristics in Turbospin at 60 LPM**

PULMONARY DELIVERY OF AMINOGLYCOSIDES

FIELD OF THE INVENTION

The present invention is directed to the administration of aminoglycosides. In particular, the present invention is directed to compositions and methods for the pulmonary administration of aminoglycosides. According to a preferred embodiment, dry powder aminoglycoside compositions and methods for their administration are provided for the localized treatment of respiratory infections.

BACKGROUND OF THE INVENTION

Aminoglycosides are potent bactericidal agents. Their main mechanism of action is on the bacterial ribosome, which in turn inhibits protein synthesis. They are active against a wide range of gram-positive and gram-negative species as well as mycobacteria. For some serious gram-negative infections, aminoglycosides or aminoglycosides in combination with other antimicrobials may be the drug of choice for Pseudonomas and other infections.

Lower respiratory tract infections with *pseudomonas aeruginosa* (Psa) are a major cause of morbidity and mortality among patients with cystic fibrosis (CF) and non-CF bronchiectasis. Once an infection is established, even aggressive antibiotic treatments may only temporarily reduce the number of Psa organisms in the respiratory tract. As a result, many CF patients have persistent Psa infections requiring frequent hospital admissions for intravenous chemotherapy.

Bronchiectasis is a condition characterized by progressive destruction and dilatation of airway walls due to infected retained secretions that result from a failure of airway defenses to maintain the sterile environment of the lower respiratory tract airways and lung parenchyma. The large volumes of infected secretions requiring aggressive antibiotic treatment at the onset of the infection and the presence of marked bacterial resistance to common and often used antibiotics represent significant barriers to effective therapy. The most effective treatment of bronchiectasis remains antibiotic therapy, usually administered systemically orally or by intravenous injection.

Aminoglycosides are considered one of the most useful classes of antibiotics for treating Psa infections. However, antibiotic therapy of a variety of respiratory infections, in particular bronchiectasis, continues to represent a major medical challenge.

One of the major disadvantages of aminoglycosides is that they can induce fairly severe side effects. Aminoglycosides are generally poorly absorbed orally and, for this reason, are given intravenously or intramuscularly. Aminoglycosides active against Psa penetrate into sputum poorly, making it necessary to administer large systemic doses intravenously in order to optimize sputum penetration at the site of infection in the lung. Such high doses can produce both nephrotic and ototoxic effects, often causing permanent renal insufficiency and auditory nerve damage, with deafness, dizziness, and unsteadiness.

At the same time, underdosing and incomplete courses of antibiotics are part of the problem of ineffective therapy. Potential consequences of underdosing respiratory tract infections include inadequate pathogen eradication, development of antibiotic resistance and lengthened eradication times, as well as potential for persistent clinical symptoms due to increasing lung injury, bronchiectasis, scarring, and premature death.

The overuse of antibiotics in the treatment of respiratory infections is a major problem and is increasingly regarded as such by both the medical community and the pharmaceutical industry. The Center for Disease Control (CDC) considers the growing problem of antibiotic resistance to be one of the most important public health challenges of our time. The CDC views overprescription of antibiotics as one of the prime culprits for the growing antibiotic resistance problem.

In view of the above problems in antibiotic therapies, research has primarily focused on the discovery of new molecules to provide possible solutions. Alternatively, the potential effectiveness of treating infections of the respiratory tract with aminoglycosides administered by new drug delivery technologies such as inhalation aerosols has been investigated. In particular, aerosolized antibiotics have been administered by small volume nebulizers (SVN) driven ultrasonically or by air compressors.

For two decades, inhaled antibiotics have been used effectively for ameliorating chronic pulmonary infections in conditions such as cystic fibrosis and non-CF bronchiectasis. To date, the U.S. Food and Drug Administration (FDA) has approved only one aerosolized antiinfective: TOBI® (Chiron Corporation, Seattle, Wash.). TOBI is a tobramycin solution for inhalation by nebulization. Tobramycin (O-3-amino-3-deoxy-α-D-glucopyranosyl-(1-4)-O-[2,6-diamino-2,3,6-trideoxy-α-D-ribo-hexopyranosyl-(1-6)]-2-deoxy-L-streptamine) is a water soluble, aminoglycoside antibiotic having a molceular weight of 467.52 g/mol. Tobramycin is effective against gram negative pathogens, in particular *Pseudomonas aeruginosa*, the key infective agent in CF patients.

The formulated TOBI product is an aqueous solution, which is sterile, clear, slightly yellow, non-pyrogenic, and is pH and salinity adjusted. It comprises 300 mg of tobramycin free base in 5 ml of sodium chloride (2.25 mg/ml) at pH 6.0 and is stable at 2-8 C. for two years, or 28 days at room temp. The solution darkens in intense light. At pH 6.0, approximately 2.2 of the 5 tobramycin amino groups have been converted to sulfate salts. A dose is a single 300 mg ampoule bid (12 hours apart).

Patients receive a 28 day "on" therapy followed by a 28 day "off" period, to reduce the potential for development of resistant bacterial strains. Of the 300 mg inhaled, only approximately 10% or 30 mg is delivered to the lung. Systemic tobramycin given by IV injection has serious adverse effects including renal and ototoxicity. High IV doses are typically given due to poor penetration of the drug across the lung endothelium and into sputum. Clinical studies with TOBI have shown that inhaled tobramycin may lead to tinitus and voice alteration.

Nebulization has many well documented disadvantages, including extended administration time, high cost, poor efficiency and reproducibility, risk of bacterial contamination, and the need for bulky compressors or gas cylinders. These disadvantages likely have an impact on patient compliance.

Pulmonary delivery by aerosol inhalation has received much attention as an attractive alternative to intravenous, intramuscular, and subcutaneous injection, since this approach eliminates the necessity for injection syringes and needles. Pulmonary delivery also limits irritation to the skin and body mucosa which are common side effects of transdermally, iontophoretically, and intranasally delivered drugs, eliminates the need for nasal and skin penetration enhancers (typical components of intranasal and transdermal systems that often cause skin irritation/dermatitis), is economically attractive, is amenable to patient self-administration, and is often preferred by patients over other alternative modes of administration. Administration of aminoglycoside dry powder aerosols to the lung has been attempted, but inefficient delivery devices and/or poorly dispersible lactose formulations limited these studies.

Dry powder inhalers are known in the art as disclosed, for example, in U.S. Pat. Nos. 5,458,135; 5,740,794; 5,775,320; and 5,785,049, and in copending U.S. application Ser. Nos. 09/004,558 filed Jan. 8, 1998, 09/312,434 filed Jun. 4, 1999, 60/136,518 filed May 28, 1999, and 60/141,793 filed Jun. 30, 1999, all of which are hereby incorporated in their entirety by reference.

In addition, U.S. Pat. No. 5,875,776 discloses a dry powder inhaler and discloses antibiotics such as gentamicin sulfate, amikacin sulfate, and tobramycin sulfate, among an extensive list of agents suitable for administration by the devices disclosed therein. No examples of formulations are disclosed. WO 00/35461 further discloses a method for treating bronchiectasis comprising the administration of an aminoglycoside aerosol.

A hollow porous tobramycin dry powder formulation was engineered and delivered from the Turbospin (PH&T, Italy) dry powder inhaler in a recent clinical study. Of the 25 mg of powder loaded into the capsule in the clinical study, only 4.6 mg (18.4%) of active drug substance was delivered to the lung. At this drug loading and efficiency, approximately 6 capsules (ca. 27.6 mg) are required to deliver a lung dose equivalent to the nebulized TOBI product. The requirement for administering at least 6 capsules raises issues with respect to patient compliance for such a therapy.

Despite the advances in discovering newer, broad spectrum antibiotics and drug delivery technologies, there remains a need for improved methods for administering antibiotics such as aminoglycosides. In particular, the maximum safe systemic dosages of aminoglycosides administered according to current therapies provide much less than the dose sufficient to achieve amounts of drug in lung tissue and secretions to exceed the minimum inhibitory capacity (i.e. concentrations capable of eliminating or significantly decreasing the bacterial burden causing the infection in the airways and lung tissues). Thus, therapy is likely to be inadequate while encouraging the emergence of resistant organisms and the development of adverse side effects. There remains a need for a patient-friendly means of administering aminoglycosides to patients which will provide higher localized concentrations of drug in the airway secretions and adjacent lung tissue without the risk of significant systemic side effects. Ideally, such administration must be from a device which is practical such that patient compliance is encouraged. The present invention meets these and other needs.

Definition of Terms

As used herein, the term "aminoglycoside" refers to both synthetic and natural antibiotics isolated from species of Streptomyces and Micromonospora as known in the art and includes, but is not limited to, gentamicin, netilmicin, tobramycin, kanamycin, neomycin, paramecin, amikacin, azithromycin and streptomycin, including pharmaceutically acceptable salts and esters thereof.

As used herein, the term "dry powder" refers to a composition that contains finely dispersed solid particles that are capable of (i) being readily dispersed in or by means of an inhalation device and (ii) inhaled by a subject so that a portion of the particles reach the lungs. Such a powder is considered to be "respirable" or suitable for pulmonary delivery. A dry powder typically contains less than about 15% moisture, preferably less than 11% moisture, and more preferably contains less than about 8% moisture.

As used herein, the term "emitted dose" or "ED" refers to an indication of the delivery of dry powder from a suitable inhaler device after a firing or dispersion event from a powder unit, capsule, or reservoir. ED is defined as the ratio of the dose delivered by an inhaler device to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing blister pack placed into an inhalation device, if dispersion of the powder results in the recovery of 4 mg of powder on a tared filter as described above, then the ED for the dry powder composition is: 4 mg (delivered dose)/5 mg (nominal dose)×100=80%.

As used herein, the term "geometric diameter" is a measure of geometric particle size and are determined using a Sympatec laser diffraction analyzer.

As used herein, the term "mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by Anderson cascade impaction.

As used herein, the term "pharmaceutically acceptable excipient or carrier" refers to an excipient that can be taken into the lungs in association with an aminoglycoside with no significant adverse toxicological effects to the subject, and particularly to the lungs of the subject.

As used herein, the term "pharmacologically effective amount" or "physiologically effective amount" is the amount of aminoglycoside present in a dry powder composition as described herein that is needed to provide a desired level of drug in the secretions and tissues of the airways and lungs, or alternatively, in the bloodstream of a subject to be treated to give an anticipated physiological response when such composition is administered pulmonarily. The precise amount will depend upon numerous factors, e.g., the particular aminoglycoside, the specific activity of the composition, the delivery device employed, physical characteristics of the powder, its intended use, and resistance of the organisms as well as patient considerations such as severity of the disease state, patient cooperation, etc., and can readily be determined by one skilled in the art, based upon the information provided herein.

As used herein, the term "respiratory infections" includes, but is not limited to upper respiratory tract infections such as sinusitis, pharyngitis, and influenza, and lower respiratory tract infections such as tuberculosis, bronchiectasis (both the cystic fibrosis and non-cystic fibrosis indications), bronchitis (both acute bronchitis and acute exacerbation of chronic bronchitis), and pneumonia (including various types of complications that arise from viral and bacterial infections including hospital-acquired and community-acquired infections).

As used herein, the term "side effects associated with aminoglycoside therapy" refers to undesirable effects suffered by a patient including, but not limited to, ototoxicity and nephrotoxicity and is further intended to include development of resistance to aminoglycoside therapy.

As used herein, the term "therapeutically effective amount" means the amount of aminoglycoside, which when delivered to the lungs and conducting airways of a subject pulmonarily via a dry powder composition as described herein, provides the desired biological effect.

BRIEF DESCRIPTION OF THE DRAWINGS

FIG. 2 depicts a plot of the emitted dose for the tobramycin formulation as a function of capsule fill mass.

FIG. 3 depicts a Plot of the Anderson Cascade Impactor particle size distribution (split flow) for a tobramycin formulation according to this invention.

SUMMARY OF THE INVENTION

Figure 1:
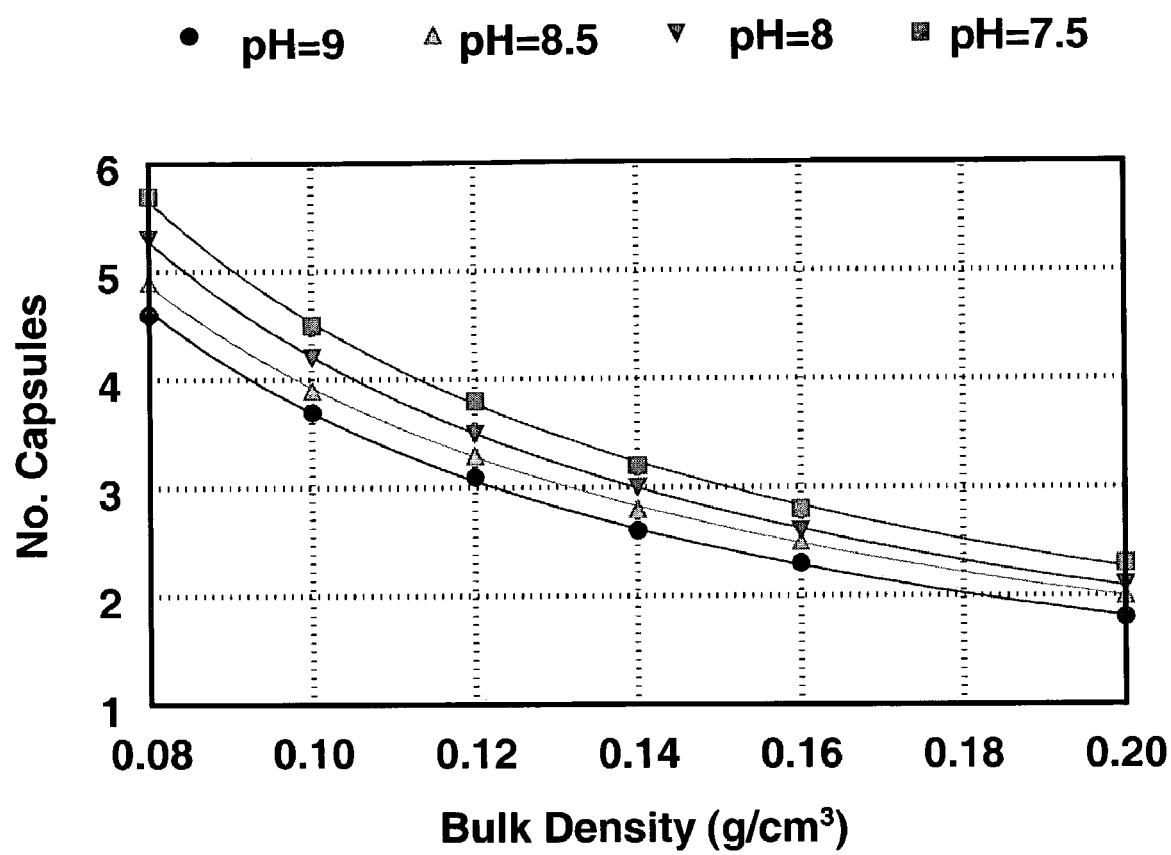
FIG. 1 depicts a plot of the number of capsules required as a function of the bulk density.

It is a general aspect of this invention to provide compositions and methods for the pulmonary administration of aminoglycoside dry powder compositions. The methods of the present invention generally provide much higher localized concentrations of aminoglycosides in the lungs for the treatment of respiratory infections without adverse systemic effects.

Thus, it is an aspect of the present invention to provide compositions and methods for the pulmonary administration of aminoglycosides.

Another aspect of this invention is to provide compositions and methods for the localized administration of aminoglycosides to the lungs for the treatment of respiratory infections.

It is yet another aspect of this invention to provide compositions and methods for pulmonary delivery of aminoglycosides for the treatment of respiratory infections with reduced side effects.

Another aspect of the present invention is directed to methods for administering aminoglycosides with reduced potential for creating resistance to the aminoglycosides.

Another aspect of the invention is directed to the administration of tobramycin as a dry powder aerosol wherein the tobramycin formulation is effective to provide a therapeutically effective therapy via administration of less than 5 capsules, preferably less than 4 capsules wherein the capsules are preferably No. 2 capsules.

Yet another aspect of the invention is to provide a reduction in the number of capsules required per dose through increases in powder density, potency, and efficiency of the formulation.

These and other aspects of the present invention will become more fully apparent in view of the following detailed description and examples.

DETAILED DESCRIPTION OF THE INVENTION

According to the present invention, compositions and methods for the pulmonary administration of aminoglycosides for the treatment of respiratory infections are provided. The pulmonary administration route offers a number of benefits, including the potential for achievement of high antibiotic concentrations in respiratory secretions while limiting systemic toxicity. The powders of the present invention exhibit outstanding aerosol characteristics without the need for blending the drug-containing powder with larger carrier particles which help enable the formulations of the present invention meet the high dosage requirements for aminoglycoside therapy with a reduced number of capsules.

Due to the relatively large dosages of aminoglycosides required for therapeutically effective treatment, the dry powder compositions of the present invention are preferably delivered from a pulmonary device at a relatively high emitted dose. According to the invention, the dry powder compositions comprise an emitted dose of at least 50%, more preferably at least 70%, and emitted doses of greater than 80% are most preferred. Such high emitted doses reduce drug costs as more efficient administration of aminoglycoside is achieved, and also improve patient compliance as fewer device actuations would be needed for effective therapy. The compositions and methods according to this embodiment of the invention provide a significant advance in the pulmonary drug delivery art as large doses of drug are capable of administration pulmonarily to provide a therapeutically effective treatment. Treatments are provided wherein a therapeutically effective amount of aminoglycoside is administered over a 24 hour administration period from a less than 5 unit doses, preferably less than 4 unit doses, in order to provide therapeutically effective therapy.

According to another embodiment of the present invention, administration methods directed at reducing side effects associated with aminoglycoside therapy are provided. These include administration of doses that are much higher than current therapies (e.g. more than 8 times MIC). According to this embodiment, problems associated with underdosing such as development of aminoglycoside resistance as discussed above are reduced. High localized concentrations of aminoglycoside in the lung without adverse side effects associated with aminoglycoside therapy are possible via pulmonary administration of the dry powder compositions of this invention.

According to another embodiment directed at reducing the development of aminoglycoside resistance, two (or perhaps more) antibiotics of different classes acting via different mechanisms are administered in rotation by inhalation.

According to the preferred embodiment, the aminoglycoside dry powder compositions are administered by inhalation via a dry powder inhaler in order to maximize dose convenience and speed of administration.

The aminoglycoside dry powder compositions of this invention generally comprise an aminoglycoside combined with one or more pharmaceutical excipients which are suitable for respiratory and pulmonary administration. Such excipients may serve simply as bulking agents when it is desired to reduce the active agent concentration in the powder which is being delivered to a patient. Such excipients may also serve to improve the dispersibility of the powder within a powder dispersion device in order to provide more efficient and reproducible delivery of the active agent and to improve the handling characteristics of the active agent (e.g., flowability and consistency) to facilitate manufacturing and powder filling. In particular, the excipient materials can often function to improve the physical and chemical stability of the aminoglycoside, to minimize the residual moisture content and hinder moisture uptake, and to enhance particle size, degree of aggregation, surface properties (i.e., rugosity), ease of inhalation, and targeting of the resultant particles to the deep lung. Alternatively, the aminoglycoside may be formulated in an essentially neat form, wherein the composition contains aminoglycoside particles within the requisite size range and substantially free from other biologically active components, pharmaceutical excipients, and the like.

Although administration via DPI is about ten times faster than via nebulizer, it would be highly advantageous from both an economic and compliance standpoint to reduce the total number of capsules needed to provide for an effective therapy via administration from a DPI from 6 to 4 or less, preferably 2 or 3. The following discussion on reducing the number of capsules for an effective aminoglycoside therapy via DPI will focus on a preferred embodiment directed to the administration of tobramycin.

The number of capsules ($n_{capsule}$) required to deliver a certain mass of drug to the lung ($m_{lung}$) can be obtained from the delivery efficiency relationship below:

$$n_{capsule} = \frac{m_{lung}}{m_{capsule} \cdot P \cdot \eta_{lung}} \quad (1)$$

where $m_{capsule}$ is the mass of powder in the capsule, P is the potency of the drug in the drug product (tobramycin free base), $\eta_{lung}$ is the efficiency of aerosol delivery to the lung.

It is clear from this relationship that the total number of capsules required can be reduced by:
(1) increasing the powder loading in the capsule;
(2) increasing the potency of drug in powder; and
(3) increasing the efficiency of aerosol delivery (emitted dose and fine particle dose)

For example, a 35 mg fill, potency of 70%, and an aerosol efficiency of 40%, one needs 2.8 capsules to deliver the 27.6 mg target lung dose. For a 40 mg fill, a potency of 80%, and an efficiency of 50%, one needs just 1.7 capsules. Preferred fill masses according to the invention are within 20-50 mg per capsule. Most preferably 25-40 mg/capsule.

Increasing the fill mass in the capsule can be accomplished by filling a greater percentage of the capsule volume, or by increasing the bulk density of the powder. Formulations according to the present invention have a bulk density of greater than 0.08 g/cm$^3$. Preferred powders according to this invention have a bulk density of 0.10 g/cm$^3$ or greater.

Theoretically, a 50 mg loading would cut the capsule requirements to 3, for a formulation with equivalent potency and aerosol performance to the tobramycin formulation used in the clinical study mentioned above. In order to achieve such a large fill mass in a number 2 capsule the powder density would need to be increased without adversely impacting aerosol characteristics. One of ordinary skill in the art can determine the bulk density at which tobramycin formulations begin to show a drop in aerosol performance in accordance with the teachings herein.

For example, the effect of bulk density on the total number of capsules required is depicted in FIG. 1. FIG. 1 is an estimate of the number of capsules required to deliver 30 mg of the free base to the lung as a function of bulk density and pH. The graph assumes that ⅔ of the capsule volume is filled with powder, that the residual moisture content is 5%, the residual solvent (PFOB) content is 0.1%, and that 40% of the nominal dose is deposited in the lungs.

The potency of tobramycin is determined by a number of factors including the drug loading in the formulation, the percentage of the primary amine groups on the free base that have been reacted with acid to form a salt, the molecular weight of the counterion (chloride or sulfate), and the residual water and blowing agent trapped in the formulation. The theoretical potency of free base in the above-mentioned clinical tobramycin formulation was 63%. The balance of mass can be attributed to the sulfate salt, where on average approximately three of the five primary amines were sulfated. The actual potency value for the tobramycin clinical formulation was 53% due to retention of residual moisture (5.3% w/w) and fluorocarbon (≈4.6% w/w) in the formulation.

Figure 4:
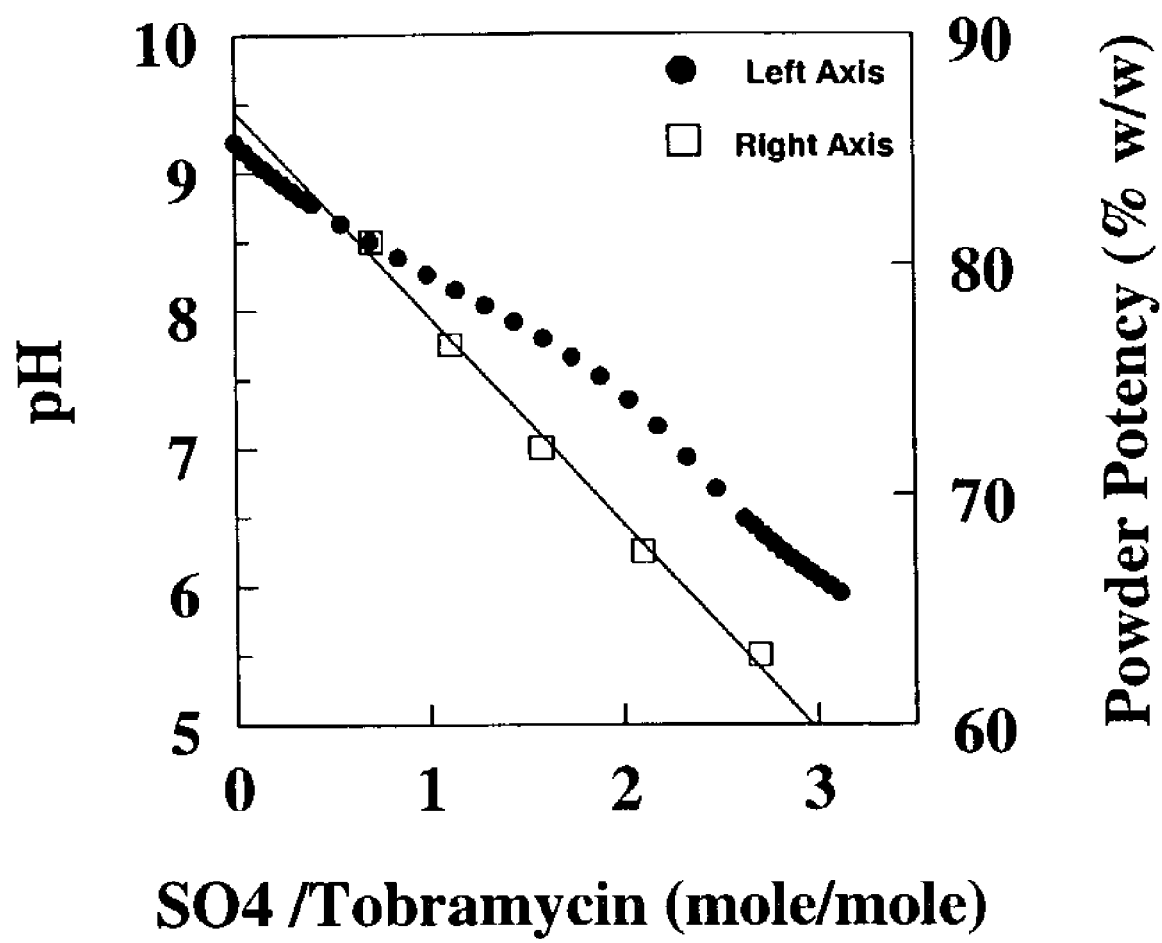
FIG. 4 depicts a titration curve for tobramycin free base with sulfuric acid. The right axis presents the theoretical powder potency for a 90% w/w formulation.

In the TOBI nebulizer product, the pH is titrated to 6.0. Adjusting the pH to 6.0 allows the product to be stable for an extended period without the addition of preservatives such as phenol. Powder formulations will not have the same stability burden, since the time in solution is short. Hence, the sulfate content can be decreased in the final product by titrating the free base to a higher pH than is used in the current TOBI product According to FIG. 4, increases in potency of greater than 60% may be possible, such as from 60% to roughly 80%.

The tobramycin formulation used in the clinical study was comprised of 90% w/w tobramycin sulfate. On average about 3 of the 5 primary amine groups on the free base are sulfated in tobramycin sulfate. From this a molecular weight for tobramycin sulfate can be estimated as follows:

Mol Wt(tobramycin sulfate)=467.54(free base)+ 3.1(96)≈765 g/mol

The same calculation can be done for the chloride salt, assuming an equal number of chloride salts per molecule:

Mol Wt(tobramycin chloride)=467.54+ 3.1(35.5)≈578 g/mol

The potential reduction in the number of capsules afforded by a switch to the chloride salt would be:

(578/765)×6 capsules=4.5 capsules (i.e., a 1.5 capsule savings)

The nature of the acid utilized: sulfuric, hydrochloric, or phosphoric, will depend not only on a desire to reduce the number of capsules, but also on the regulatory impact of changing acid, and the variations in solid state and aerosol performance noted.

Improvements of the aerosol characteristics also contribute to a reduction in the number of capsules necessary for an effective therapy.

Pharmaceutical excipients and additives useful in the present composition include but are not limited to proteins, peptides, amino acids, lipids, polymers, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which may be present singly or in combination. Exemplary protein excipients include serum albumin such as human serum albumin (HSA), recombinant human albumin (rHA), gelatin, casein, and the like. Representative amino acid/polypeptide components, which may also function in a buffering capacity, include alanine, glycine, arginine, betaine, histidine, glutamic acid, aspartic acid, cysteine, lysine, leucine, proline, isoleucine, valine, methionine, phenylalanine, aspartame, and the like. Polyamino acids of the representative amino acids such as di-leucine and tri-leucine are also suitable for use with the present invention. One preferred amino acid is leucine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like.

The dry powder compositions may also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, the aminoglycoside dry powders of the invention may include polymeric excipients/additives such as polyvinylpyrrolidones, hydroxypropyl methylcellulose, methylcellulose, ethylcellulose, Ficolls (a polymeric sugar), dextran, dextrates (e.g., cyclodextrins, such as 2-hydroxypropyl-β-cyclodextrin, hydroxyethyl starch), polyethylene glycols, pectin, flavoring agents, salts (e.g. sodium chloride), antimicrobial agents, sweeteners, antioxidants, antistatic agents, surfactants (e.g., polysorbates such as "TWEEN 20" and "TWEEN 80", lecithin, oleic acid, benzalkonium chloride, and sorbitan esters), lipids (e.g., phospholipids, fatty acids ), steroids (e.g., cholesterol), and chelating agents (e.g., EDTA). Other pharmaceutical excipients and/or additives suitable for use in the aminoglycoside compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), the disclosures of which are herein incorporated by reference.

According to the present invention, a dispersing agent for improving the intrinsic dispersibility properties of the aminoglycoside powders is added. Suitable agents are disclosed in PCT applications WO 95/31479, WO 96/32096, and WO 96/32149, hereby incorporated in their entirety by reference. As described therein, suitable agents include water soluble polypeptides and hydrophobic amino acids such as tryptophan, leucine, phenylalanine, and glycine. Leucine and tri-leucine are particularly preferred for use according to this invention.

In accordance with the invention, the solid state matrix formed by the aminoglycoside and excipient imparts a stabilizing environment to the aminoglycoside. The stabilizing matrix may be crystalline, an amorphous glass, or a mixture of both forms. Most suitable are dry powder formulations which are a mixture of both forms. For aminoglycoside dry powder formulations which are substantially amorphous, preferred are those formulations exhibiting glass transition temperatures ($T_g$) above about 35° C., preferably above about 45° C., and more preferably above about 55° C. Preferably, $T_g$ is at least 20° C. above the storage temperature. According to a preferred embodiment, the aminoglycoside formulations comprise a phospholipid as the solid state matrix as disclosed in WO 99/16419 and WO 01/85136, hereby incorporated in their entirety by reference.

The aminoglycoside contained in the dry powder formulations is present in a quantity sufficient to form a pharmacologically-effective amount when administered by inhalation to the lung. The dry powders of the invention will generally contain from about 20% by weight to about 100% by weight aminoglycoside, more typically from about 50% to 99% by weight aminoglycoside, and preferably from about 80 to 95% by weight aminoglycoside. Correspondingly, the amount of excipient material(s) will range up to about 80% by weight, more typically up to about 50% by weight, and preferably from about 20 to 5% by weight.

In one preferred embodiment of the invention, the dry powder contains at least 80% by weight aminoglycoside in order to provide a unit dose effective to administer up to 100 mg, preferably from 10-60 mg/unit dose with the appropriate dose adjusted for the particular aminoglycoside as readily determined by one of ordinary skill.

Preparation of Aminoglycoside Dry Powders

Dry powder aminoglycoside formulations may be prepared by spray drying under conditions which result in a substantially amorphous glassy or a substantially crystalline bioactive powder as described above. Spray drying of the aminoglycoside-solution formulations is carried out, for example, as described generally in the "Spray Drying Handbook", $5^{th}$ ed., K. Masters, John Wiley & Sons, Inc., NY, N.Y. (1991), and in WO 97/41833, the contents of which are incorporated herein by reference.

To prepare an aminoglycoside solution for spray drying according to one embodiment of the invention, an aminoglycoside is generally dissolved in a physiologically acceptable solvent such as water. The pH range of solutions to be spray-dried is generally maintained between about 3 and 10, preferably 5 to 8, with near neutral pHs being preferred, since such pHs may aid in maintaining the physiological compatibility of the powder after dissolution of powder within the lung. The aqueous formulation may optionally contain additional water-miscible solvents, such as alcohols, acetone, and the like. Representative alcohols are lower alcohols such as methanol, ethanol, propanol, isopropanol, and the like. Aminoglycoside solutions will generally contain aminoglycoside dissolved at a concentration from 0.05% (weight/volume) to about 20% (weight/volume), usually from 0.4% to 5.0% (weight/volume).

The aminoglycoside-containing solutions are then spray dried in a conventional spray drier, such as those available from commercial suppliers such as Niro A/S (Denmark), Buchi (Switzerland) and the like, resulting in a stable, aminoglycoside dry powder. Optimal conditions for spray drying the aminoglycoside solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause deactivation of aminoglycoside in the sprayed material. Such temperatures are typically determined experimentally, although generally, the inlet temperature will range from about 50° C. to about 200° C. while the outlet temperature will range from about 30° C. to about 150° C.

Alternatively, aminoglycoside dry powders may be prepared by lyophilization, vacuum drying, spray freeze drying, super critical fluid processing, or other forms of evaporative drying or by blending, grinding or jet milling formulation components in dry powder form. In some instances, it may be desirable to provide the aminoglycoside dry powder formulation in a form that possesses improved handling/processing characteristics, e.g., reduced static, better flowability, low caking, and the like, by preparing compositions composed of fine particle aggregates, that is, aggregates or agglomerates of the above-described aminoglycoside dry powder particles, where the aggregates are readily broken back down to the fine powder components for pulmonary delivery, as described, e.g., in U.S. Pat. No.

5,654,007, incorporated herein by reference. Alternatively, the aminoglycoside powders may be prepared by agglomerating the powder components, sieving the materials to obtain the agglomerates, spheronizing to provide a more spherical agglomerate, and sizing to obtain a uniformly-sized product, as described, e.g., in WO 95/09616, incorporated herein by reference. The aminoglycoside dry powders are preferably maintained under dry (i.e., relatively low humidity) conditions during manufacture, processing, and storage.

According to a preferred embodiment, the aminoglycoside powders are made according to the emulsification/spray drying process disclosed in WO 99/16419 and WO 01/85136 cited above. Formulations according to such preferred embodiments are engineered to comprise dry powder particulates comprising at least 75% w/w, preferably at least 85% w/w tobramycin, 2-25% w/w of a phospholipid, preferably 8-18% w/w, and 0-5% w/w of a metal ion such as calcium chloride. The particulates comprise a geometric diameter of less than 5 microns, an MMAD of less than 5 microns, preferably 1-4 microns, and a bulk density of greater than 0.08 g/cm$^3$, preferably greater than 0.12 g/cm$^3$.

Aminoglycoside Dry Powder Characteristics

It has been found that certain physical characteristics of the aminoglycoside dry powders, to be described more fully below, are important in maximizing the efficiency of aerosolized delivery of such powders to the lung.

The aminoglycoside dry powders are composed of particles effective to penetrate into the lungs, that is, having a geometric diameter of less than about 10 µm, preferably less than 7.5 µm, and most preferably less than 5 µm, and usually being in the range of 0.1 µm to 5 µm in diameter. Preferred powders are composed of particles having a geometric diameter from about 0.5 to 4.0 µm.

The aminoglycoside powders of the invention are further characterized by an aerosol particle size distribution less than about 10 µm mass median aerodynamic diameter (MMAD), and preferably less than 5.0 µm. The mass median aerodynamic diameters of the powders will characteristically range from about 0.5-10 µm, preferably from about 0.5-5.0 µm MMAD, more preferably from about 1.0-4.0 µm MMAD. To further illustrate the ability to prepare aminoglycoside powders having an aerosol particle size distribution within a range suitable for pulmonary administration, exemplary aminoglycoside dry powders are composed of particles having an aerosol particle size distribution less than about 5 µm MMAD, and more specifically, characterized by MMAD values less than 4.0 µm.

The aminoglycoside dry powders generally have a moisture content below about 15% by weight, usually below about 11% by weight, and preferably below about 8% by weight. The moisture content of representative aminoglycoside dry powders prepared as described herein is provided in the Examples.

The emitted dose (ED) of these powders is greater than 50%. More preferably, the ED of the aminoglycoside powders of the invention is greater than 70%, and is often greater than 80%. In looking at the Examples, it can be seen that applicants have successfully prepared a large number of representative aminoglycoside dry powders with ED values greater than or equal to 80%.

Pulmonary Administration

The aminoglycoside dry powder formulations described herein may be delivered using any suitable dry powder inhaler (DPI), i.e., an inhaler device that utilizes the patient's inhaled breath as a vehicle to transport the dry powder drug to the lungs. Preferred dry powder inhalation devices are described in U.S. Pat. Nos. 5,458,135; 5,740,794; 5,775, 320; and 5,785,049, and in copending U.S. application Ser. Nos. 09/004,558 filed Jan. 8, 1998, 09/312,434 filed Jun. 4, 1999, 60/136,518 filed May 28, 1999, and 60/141,793 filed Jun. 30, 1999, listed above. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities with metered doses of dry powder medicament are described in U.S. Pat. No. 5,826,633, incorporated herein by reference.

Also suitable for delivering the aminoglycoside powders described herein are dry powder inhalers of the type described, for example, in U.S. Pat. Nos. 3,906,950 and 4,013,075, 4,069,819, and 4,995,385, incorporated herein by reference, wherein a premeasured dose of aminoglycoside dry powder for delivery to a subject is contained within a capsule such as a hard gelatin capsule or HPMC capsule. HPMC capsules are preferred, preferably size #2 capsules containing up to 50 mg powder, preferably 20-40 mg. It is to be understood that other sized capsules, such as 00, 0, No. 1, or No. 3 sized capsules are also suitable for use with the present invention and their suitability depends, among other factors, upon the inhalation device used to administer the powders.

Other dry powder dispersion devices for pulmonarily administering aminoglycoside dry powders include those described, for example, in EP 129985; EP 472598; EP 467172; and U.S. Pat. No. 5,522,385, incorporated herein in their entirety by reference. Also suitable for delivering the aminoglycoside dry powders of the invention are inhalation devices such as the Astra-Draco "TURBUHALER". This type of device is described in detail in U.S. Pat. Nos. 4,668,218; 4,667,668; and 4,805,811, all of which are incorporated herein by reference.

Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in U.S. Pat. No. 5,388,572, incorporated herein by reference.

Prior to use, the aminoglycoside dry powders are generally stored in a receptacle under ambient conditions, and preferably are stored at temperatures at or below about 30° C., and relative humidities (RH) ranging from about 30 to 60%. More preferred relative humidity conditions, e.g., less than about 30%, may be achieved by the incorporation of a dessicating agent in the secondary packaging of the dosage form.

The following examples are offered by way of illustration, not by way of limitation. The following materials were used in the Examples (the grades and manufacturers are representative of many that are suitable):

Gentamicin Sulfate (H&A (Canada) Industrial)
Netilmicin Sulfate (Scientific Instruments And Technology)
Tobramycin (Chiron, Berkeley, Calif.)
L-Leucine (Aldrich)
Hydrochloric Acid (J. T. Baker)
Sodium Hydroxide 0.1N Volumetric Solution (J. T. Baker)

Ethanol, 200 proof (USP/NF, Spectrum Chemical Mfg. Corp.)
Methanol (HPLC grade, EM Industries)

EXAMPLE 1

A. Formulation

Dry powder compositions containing gentamicin were prepared by mixing gentamicin sulfate and excipient(s) (if used) with a liquid medium to form a solution. The pH of the solution was adjusted as appropriate to facilitate solubilization and/or stabilization of the components in the solution. Quantitative formulations are identified in Table 1 below.

B. Spray Drying

The gentamicin solutions were spray dried on Buchi 190 Mini Spray Dryers, with nozzles and cyclones that were designed to generate and catch very fine particles. For formulations that utilized organic solvents, a modified Buchi 190 Mini Spray Dryer was used that was supplied with nitrogen as the gas source and equipped with an oxygen sensor and other safety equipment to minimize the possibility of explosion. The solution feed rate was 5 ml/minute, solution was maintained at room temperature, inlet temperature range was 120-131° C. and was adjusted to obtain an outlet temperature of approximately 80° C., the drying gas flow rate was about 18 SCFM, and the atomizing air was supplied at 0.5 to 1.5 SCFM, typically at a pressure of about 100 PSI.

C. Characterization

Each powder was characterized in terms of moisture content, emitted dose (ED), and mass median aerodynamic diameter (MMAD). ED is a measure of efficiency for the powder package/device combination. MMAD refers to a measure of the particle size of the aerosolized powder.

Moisture content was determined by the Karl-Fischer Reagent titrimetric method or by thermogravimetric analysis as indicated in the following tables.

Morphology was determined by scanning electron microscopy (SEM).

To determine the ED, the spray dried powders were first filled into blister packs. The test was performed by connecting a vacuum system to the mouthpiece of an inhaler device of the type describe in U.S. Pat. No. 5,740,794 identified above. The vacuum system was set to be similar to a human inhalation with regard to volume and flow rate (1.2 liters total at 30 liters/minute). A blister package containing 5 mg of the formulation to be evaluated was loaded into a device, which was held in a testing fixture. The device was pumped and fired, and the vacuum "inhalation" switched on. The aerosol cloud was drawn out of the device chamber by the vacuum, and the powder was collected on a filter placed between the mouthpiece and the vacuum source. The weight of the powder collected on the filter was determined. Emitted dose was calculated as this weight, multiplied by one hundred, divided by the fill weight in the blister. A higher number is a better result than a lower number.

MMAD was determined with an Andersen cascade impactor. In a cascade impactor the aerosolized powder (which was aerosolized using an inhaler device as described in U.S. Pat. No. 5,740,794) enters the impactor via an air stream, and encounters a series of stages that separate particles by their aerodynamic diameter (the smallest particles pass farthest down the impactor). The amount of powder collected on each stage was determined gravimetrically, and the mass median aerodynamic diameter was then calculated.

Tables 1 show the quantitative composition of gentamicin formulations, a description of the particle morphology, moisture content, MMAD, and emitted dose of the resultant gentamicin powders.

TABLE 1

Gentamicin Dry Powder Compositions

| Batch Number | Quantitative Composition | Particle Morphology | Moisture Content | MMAD (μm) | Emitted Dose |
|---|---|---|---|---|---|
| 1326-31 | Gentamicin sulfate 2076 mg<br>DI water 200 ml<br>Hydrochloric acid QS to pH = 5 | Smooth spheres sometimes with a large dimple or two | 4.1%[1] | 3.0 | 37% (RSD[3] = 6) |
| 1326-32 | Gentamicin sulfate 2053 mg<br>DI water 200 ml<br>Sodium hydroxide QS to pH = 10 | Slightly dimpled spheres | 1.1%[1] | 2.4 | 40% (RSD = 14) |
| 1300-MG-11 | Gentamicin sulfate 2012 mg<br>Ethanol 40 ml<br>DI water 160 ml | Smooth spheres sometimes with a large dimple or two | 4.8%[2] | 3.0 | 45% (RSD = 10) |
| 1300-MG-12 | Gentamicin sulfate 2006 mg<br>L-leucine 205 mg<br>DI water 20 ml | Highly dimpled spheres | 6.2%[2] | 2.6 | 61% (RSD = 7) |
| 1300-MG-18 | Gentamicin sulfate 1500 mg<br>L-leucine 510 mg<br>DI water 200 ml | Raisin-like | 4.3%[2] | 2.4 | 80% (RSD = 6) |

[1]Determined with Karl-Fischer reagent titrimetric method
[2]Determined with thermogravimetric analysis
[3]Relative Standard Deviation

EXAMPLE 2

Formulations containing netilmicin were prepared according to the procedure set forth in Example 1. The netilmicin formulations were spray dried and characterized as set forth in Example 1. Results are set forth in Table 2 below.

TABLE 2

Netilmicin Dry Powder Compositions

| Batch Number | Quantitative Composition | Particle Morphology | Moisture Content[1] | MMAD (μm) | Emitted Dose |
|---|---|---|---|---|---|
| 1300-MG-9 | Netilmicin Sulfate 1626 mg<br>DI water 163 ml | Irregular and jagged | 4.2% | 3.2 | 47% (RSD = 8) |
| 1300-MG-14 | Netilmicin Sulfate 1512 mg<br>Ethanol 30 ml<br>DI water 120 ml | Smooth spheres often with a single or a few large dimples | 5.1% | 2.9 | 39% (RSD = 7) |
| 1300-MG-15 | Netilmicin Sulfate 1202 mg<br>L-leucine 393 mg<br>DI water 160 ml | Raisin-like | 4.1% | 2.3 | 78% (RSD = 10) |
| 1300-MG-19 | Netilmicin Sulfate 1426 mg<br>L-leucine 77 mg<br>DI water 150 ml | Dimpled Spheres | 5.3% | 2.6 | 75% (RSD = 6) |

[1]Determined with thermogravimetric analysis

EXAMPLE 3

The procedures set forth in Example 1 were repeated for the aminoglycoside tobramycin. Results are represented in Table 3 below.

TABLE 3

Tobramycin Dry Powder Compositions

| Batch Number | Quantitative Composition | Particle Morphology | Moisture Content[1] | MMAD (μm) | Emitted Dose |
|---|---|---|---|---|---|
| 1504-HS-7 | Tobramycin 2.04 g<br>DI water 204 ml | Not available | 3.9% | 2.3 | 32% (RSD = 8) |
| 1504-HS-9 | Tobramycin 1.50 g<br>L-Leucine 0.51 g<br>DI water 200 ml | Dimpled spheres | 2.6% | 2.3 | 72% (RSD = 5) |
| 1504-HS-39 | Tobramycin 1.50 g<br>L-Leucine 0.51g<br>DI water 200 ml<br>Sulfuric acid to adjust solution to pH = 5.5 | Dimpled spheres | 5.4% | 2.4 | 73% (RSD = 5) |

[1]Determined with thermogravimetric analysis

EXAMPLE 2

Powder Manufacture

Tobramycin sulfate formulations set forth in Table 4 below was manufactured according to the following procedure. SWFI was heated above the gel to liquid crystal temperature of disteroyl phosphatidylcholine (DSPC) (≈80° C.). DSPC and calcium chloride dihydrate were then added to the heated water. The resulting lipid dispersion was mixed in an UltraTurrax T-50 (IKA Labortechnik) at 8,000 rpm for 5 min. Perfluorooctyl bromide (PFOB) was then added dropwise (15 ml min$^{-1}$) to the lipid dispersion under mixing. After the addition was complete the resulting PFOB-in-water emulsion was mixed for an additional 10 min at 10,000 rpm. Emulsification in the UltraTurrax produces droplets in the micron-size range. Tobramycin sulfate was then dissolved in the continuous phase of the emulsion and the resulting dispersion was used as the feedstock for spray drying.

The feedstock was then spray dried using the equipment and conditions set forth in Table 5 below.

TABLE 4

Tobramycin Sulfate Formulation.

| Tobramycin Sulfate | 90.04% w/w |
|---|---|
| DSPC | 9.56% w/w |

TABLE 4-continued

Tobramycin Sulfate Formulation.

| | |
|---|---|
| CaCl$_2$ | 0.40% w/w |
| PFOB, φ | 0.198 v/v |
| PFOB/Total Solids | 6.37% w/w |
| Feed Concentration | 5.92% w/v |

TABLE 5

Spray drying Equipment and Conditions.

| Lot # | 2715-08 | 2792-11 | 2792-12 |
|---|---|---|---|
| Spray Dryer: | Buchi | NIRO | NIRO |
| Drying Gas | CDA | Room Air | Room Air |
| Gauge Conditions: | | | |
| Total Air Flow (SCFM) | 12 | 70 | 70 |
| Inlet Temperature (° C.) | 85 | 140 | 112 |
| Outlet Temperature (° C.) | 62 | 76 | 54 |
| Pump Rate (mL/min) | 2.1 | 35 | 35 |
| Atomizer Pressure (psi) | 11 | 100 | 100 |
| Atomizer Flow Rate (SCFM) | 2.8 | 12 | 12 |

Hand-Filling: The powder was hand filled into #2 HPMC capsules for aerosol testing. Capsules were allowed to equilibrate at <5% RH overnight. Powders were placed into a capsule filling station with relative humidity of 10 to 15% and allowed to equilibrate for 10 minutes prior to handling. Fill weights ranging from 20 mg to 40 mg were explored, representing fill volumes of approximately ½ to ⅞. Aerosol testing was performed using a Turbospin® (PH&T, Italy) capsule based passive delivery device. The filled capsules were tested the day of filling.

Particle Size Analysis by Laser Diffraction: The geometric particle size analysis of the powders were determined using a Sympatec laser diffraction analyzer (HELOS H1006, Clausthal-Zellerfeld, Germany) equipped with a RODOS type T4.1 vibrating trough. Approximately 2 mg of bulk powder was emptied onto the RODOS vibrating trough, which was subsequently atomized through a laser beam using 1 bar of air pressure, 53 mbar of vacuum, 70% feed rate, 1.30 mm funnel gap with the R2 lens setting. Data was collected over an interval of 0.4 s, with a 175 μm focal length, triggered at 0.1% obscuration. Particle size distributions were determined using the Fraünhofer model.

Residual Moisture: The residual moisture in the bulk powder was determined by Karl Fisher titrimetry.

The Emitted Dose Testing: This measurement was performed using the medium resistance Turbospin device operated at its optimal sampling flow rate of 60 L·min$^{-1}$. A total of 10 measurements was determined for each fill mass explored. Results are depicted in FIG. 2, which shows emitted dose results for the same formulation at fill masses as high as 40 mg. No significant decreases in ED or increases in RSD are noted. Increasing the powder load by 25% to 35% (with equivalent aerosol performance) results in a capsule savings of about 2 capsules, dropping the capsule needs from 6 to 4.

Aerodynamic Particle Size Distribution: Aerodynamic particle size distributions were determined gravimetrically on an Andersen cascade impactor (ACI). Particle size distributions were measured at a flow rates 56.6 L·min$^{-1}$ (i.e., forceful inhalation effort) using the Turbospin DPI device. Results are depicted in FIG. 3, which shows a plot of the aerosol particle size distribution as a function of a capsule fill mass. It is clear that a significant increase in capsule fill mass is achievable without significant variations in the aerodynamic particle size distribution.

It is claimed:

1. A composition for delivery of aminoglycoside to the lungs, the composition comprising a volume of particles that forms a respirable unit dose, the particles comprising aminoglycoside, a bulk density of greater than 0.08 g/cm$^3$, a geometric diameter of less than 5 microns, and a mass median aerodynamic diameter of less than 5 microns;
    wherein the volume of particles that forms a respirable unit dose is equivalent to, or less than, a capsule volume corresponding to a size #00 capsule, and
    wherein administration of less than 6 of the respirable unit doses is effective to provide at least 27.6 mg of aminoglycoside to the lungs.

2. A composition according to claim 1 wherein the particles comprise a pharmaceutically acceptable excipient.

3. A composition according to claim 2 wherein the pharmaceutically acceptable excipient comprises a dispersing agent selected from the group consisting of hydrophobic amino acids and water soluble polypeptides.

4. A composition according to claim 3 wherein the dispersing agent comprises a hydrophobic amino acid selected from the group consisting of alanine, isoleucine, leucine, methionine, phenylalanine, proline, tryptophan, valine and combinations thereof.

5. A composition according to claim 3 wherein the dispersing agent comprises leucine.

6. A composition according to claim 1 wherein the aminoglycoside comprises a potency of greater than 60%.

7. A composition according to claim 1 wherein the aminoglycoside is selected from the group consisting of gentamicin, netilmicin, paramecin, tobramycin, amikacin, kanamycin, neomycin, streptomycin and their salts and combinations thereof.

8. A composition according to claim 1 having a residual moisture content of below about 15% by weight.

9. A composition according to claim 1 wherein the particles have a geometric diameter from 0.5-5 microns.

10. A composition according to claim 1 wherein the mass median aerodynamic diameter is from 1-4 microns.

11. A composition according to claim 1 wherein the respirable unit dose provides an emitted dose of at least 70%.

12. A composition According to claim 1 wherein the aminoglycoside comprises at least 75% w/w tobramycin or salt thereof.

13. A composition according to claim 1 wherein the aminoglycoside comprises at least 85% w/w tobramycin or salt thereof.

14. A composition according to claim 12 further comprising up to 20% w/w of a phospholipid.

15. A composition according to claim 12 wherein the particles comprise a bulk density of greater than 0.10 g/cm$^3$.

16. A composition according to claim 1 wherein the particles comprise a hollow and porous morphology.

17. A composition according to claim 12 comprising a tobramycin potency of greater than 60%.

18. A spray dried composition according to claim 1 wherein the particles are formed by spray drying.

19. A method for administering aminoglycoside to the lungs, said method comprising administering by inhalation the composition of claim 1 in aerosolized form.

20. A method for administering aminoglycoside to the lungs, said method comprising administering by inhalation the composition of claim 5 in aerosolized form.

21. The composition of claim 19 wherein said composition is administered by an inhaler device.

22. A respirable composition comprising a volume of particles for delivery of aminoglycoside to the lungs of a patient,
the particles comprising (i) aminoglycoside, (ii) phospholipid, (iii) a bulk density of greater than 0.08 g/cm$^3$, (iv) a geometric diameter of 1 to 5 microns, and (v) a mass median aerodynamic diameter of less than 5 microns,
wherein the volume of particles forms a respirable unit dose and the volume of particles is equivalent to, or less than, a capsule volume corresponding to a size #2 capsule, and
wherein administration of less than 6 of the respirable unit doses to the patient is effective to provide at least 27.6 mg of aminoglycoside to the lungs of the patient.

23. A composition according to claim 22 wherein the composition comprises a bulk density of greater than 0.10 g/cm$^3$.

24. A composition according to claim 22 capable of providing at least 27.6 mg of the aminoglycoside to the lungs via 4 respirable unit doses or less.

25. A composition according to claim 22 wherein the aminoglycoside or salt thereof is present in an amount corresponding to 10-60 mg/unit dose.

26. A composition according to claim 22 wherein the aminoglycoside or salt thereof is present in an amount of at least 50% by weight.

27. A composition according to claim 22 wherein the aminoglycoside or salt thereof is present in an amount of at least 80% by weight.

28. A composition according to claim 22 wherein the aminoglycoside is selected from the group consisting of gentamicin, netilmicin, paramecin, tobramycin, amikacin, kanamycin, neomycin, streptomycin and their salts and combinations thereof.

29. A composition according to claim 22 wherein the aminoglycoside comprises at least 75% w/w tobramycin or salt thereof.

30. A composition according to claim 22 wherein the particles comprise 2-25 w/w % of the phospholipid.

31. A composition according to claim 22 wherein the particles comprise a metal ion.

32. A composition according to claim 22 wherein the particles comprise calcium chloride.

33. A composition according to claim 22 wherein the particles comprise spray dried particles having a hollow and porous morphology.

34. A composition according to claim 22 wherein the fill mass of the composition in a unit dose capsule is within 20-100 mg per capsule.

35. A composition according to claim 22 wherein the fill mass of the composition in a unit dose capsule is within 25-60 mg per capsule.

36. A method for administering an aminoglycoside to the lungs, said method comprising administering by inhalation the composition of claim 22 in aerosolized form.

37. A method for administering an aminoglycoside to the lungs to reduce the potential for development of bacteria in the lungs, the method comprising administering by inhalation the composition of claim 22 in aerosolized form, in a course of treatment which is performed over a plurality of days.

38. A composition for delivery of aminoglycoside to the lungs, the composition comprising a volume of particles that forms a respirable unit dose, the particles comprising aminoglycoside, a bulk density of greater than 0.08 g/cm$^3$, a geometric diameter of less than 5 microns and a mass median aerodynamic diameter of from 1-4 microns;
wherein the volume of particles that forms a respirable unit dose is equivalent to, or less than, a capsule volume corresponding to a size #00 capsule, and
wherein administration of less than 6 of the respirable unit doses provides a therapeutically effective dosage of aminoglycoside to the lungs.

39. A composition according to claim 38 wherein the aminoglycoside comprises a potency of greater than 60%.

40. A composition according to claim 38 wherein the aminoglycoside is selected from the group consisting of gentamicin, netilmicin, paramecin, tobramycin, amikacin, kanamycin, neomycin, streptomycin and their salts and combinations thereof.

41. A composition according to claim 38 wherein the particles have a residual moisture content of below about 15% by weight.

42. A composition according to claim 38 wherein the particles have a geometric diameter from 0.5-5 microns.

43. A composition according to claim 38 wherein the aminoglycoside comprises at least 75% w/w tobramycin or salt thereof.

44. A composition according to claim 38 wherein the particles comprise up to 20% w/w of a phospholipid.

45. A composition according to claim 38 wherein the particles comprise a hollow and porous morphology.

46. A composition according to claim 38 wherein the aminoglycoside comprises tobramycin in a potency of greater than 60%.

47. A spray dried composition according to claim 38 wherein the particles are formed by spray dying.

48. A method for administering aminoglycoside to the lungs, the method comprising administering by inhalation the composition of claim 38 in aerosolized form.

49. The method of claim 48 wherein the composition is administered in aerosolized form by an inhaler device.

* * * * *